US00PP32742P3

(12) United States Plant Patent
Testolin et al.

(10) Patent No.: US PP32,742 P3
(45) Date of Patent: Jan. 12, 2021

(54) KIWI PLANT NAMED 'AC 501 022'

(50) Latin Name: ***Actinidia chinensis* Planch.**
Varietal Denomination: AC 501 022

(71) Applicant: Università degli Studi di Udine, Udine (IT)

(72) Inventors: Raffaele Testolin, Udine (IT); Guido Cipriani, Faedis (IT)

(73) Assignee: Università degli Studi Udine, Udine (IT)

( * ) Notice: Subject to any disclaimer, the term of this patent is extended or adjusted under 35 U.S.C. 154(b) by 0 days.

(21) Appl. No.: 16/602,861

(22) Filed: Dec. 11, 2019

(65) Prior Publication Data

US 2020/0196499 P1 Jun. 18, 2020

(30) Foreign Application Priority Data

Dec. 14, 2018 (QZ) ..... PBR 2018/3379

(51) Int. Cl.
*A01H 5/08* (2018.01)
*A01H 6/00* (2018.01)

(52) U.S. Cl.
USPC ..... Plt./156
CPC ..... *A01H 6/00* (2018.05); *A01H 5/08* (2013.01)

(58) Field of Classification Search
USPC ..... Plt./156
See application file for complete search history.

*Primary Examiner* — Susan McCormick Ewoldt
(74) *Attorney, Agent, or Firm* — Michelle Bos Legal LLC

(57) ABSTRACT

A new female kiwi plant named 'AC 501 022', distinguished by its oblong fruit with dark brown hairless skin and yellow flesh. The fruit is very sweet with low acidity, and matures relatively early.

4 Drawing Sheets

Genus and species: *Actinidia chinensis* Planch.
Variety denomination: 'AC 501 022'.

BACKGROUND AND SUMMARY OF THE NEW VARIETY

The invention relates to a new variety of kiwi plant (*Actinidia chinensis* Planch.) named 'AC 501 022', which originated in the course of a plant breeding program at Udine, Italy. Female parent 'Ac328.26' (not patented) was crossed with male parent 'A134.41' (not patented), and 'AC 501 022' was selected from the resulting seedlings. The new variety has been asexually reproduced by grafting and by in vitro propagation at Bernalda-Metaponto, Matera, Italy, and has been found to remain true-to-type over successive generations.

'AC 501 022' is distinguished from parent variety 'Ac328.26' and similar variety 'Soreli' (U.S. Plant Pat. No. 21,552) by the characteristics set forth in Table 1 below.

TABLE 1

Comparison of 'AC 501 022' to 'Ac328.26' and 'Soreli'

| | 'AC 501 022' | 'Ac328.26' | 'Soreli' |
|---|---|---|---|
| Plant vigor | Strong | Medium | Weak |
| Bud burst | Late | Late | Intermediate |
| Leaf basal lobes | Absent | Touching | Slightly overlapping |
| Harvest time | Early | Late | Early |
| Suitability for storage | Long storage | Long storage | Medium storage |

'AC 501 022' is further distinguished from 'Soreli' by the characteristics set forth in Table 2 below.

TABLE 2

Comparison of 'AC 501 022' to 'Soreli'

| | 'AC 501 022' | 'Soreli' |
|---|---|---|
| Density of hair on young shoot | Very sparse | Medium |
| Color of stem shoot on sunny side | Grey brown | Purple brown |
| Shape of leaf apex | Retuse | Acuminate |

DESCRIPTION OF THE PHOTOGRAPHS

Figure 1:
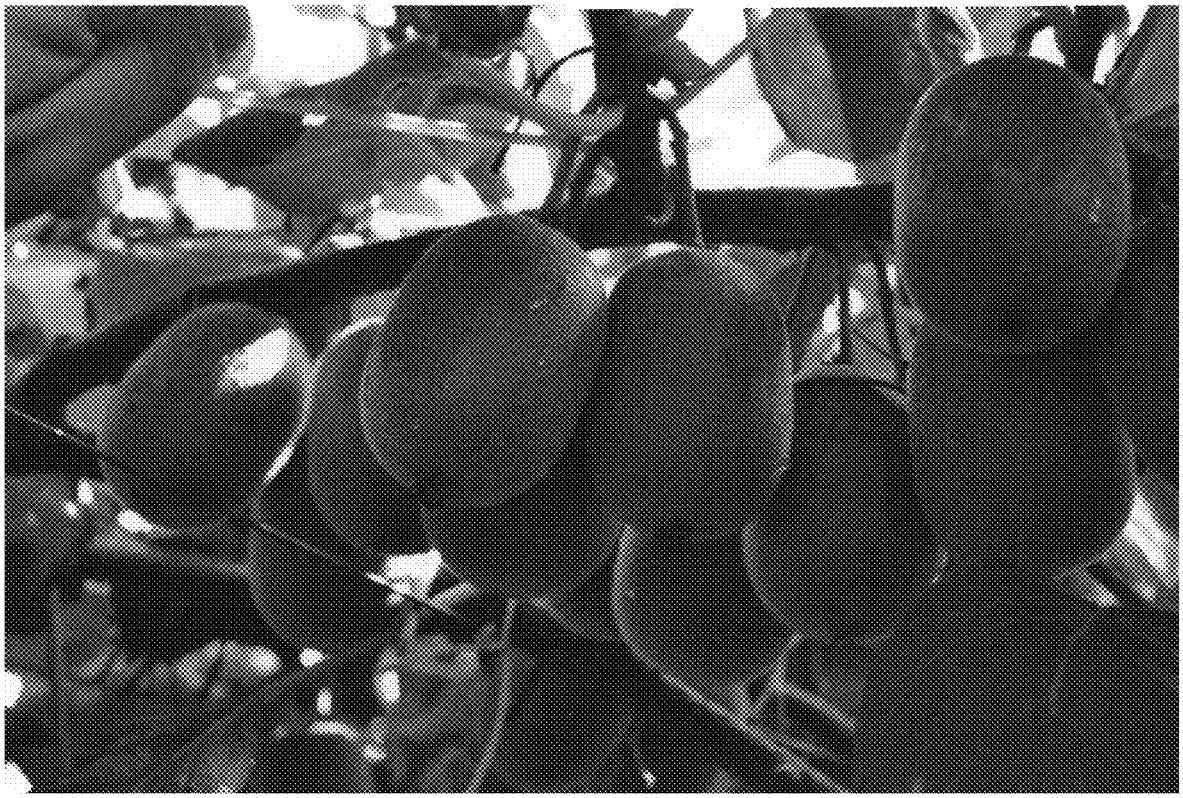
Figure 2:
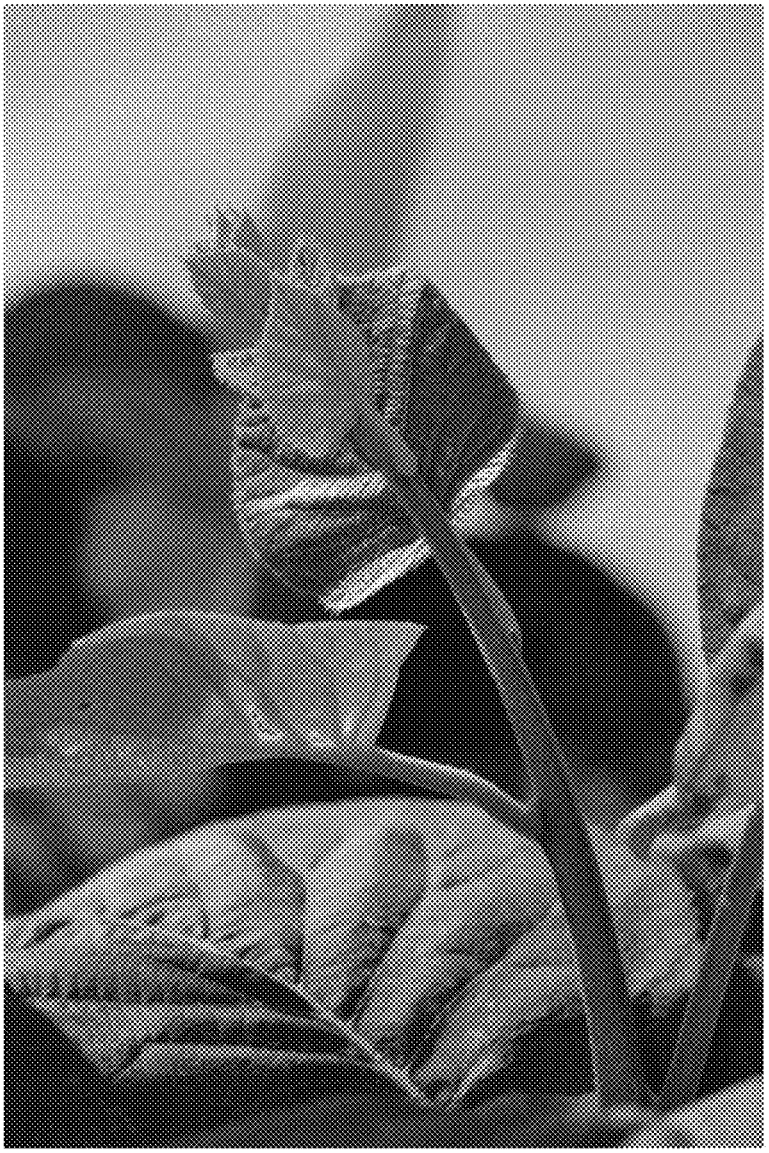
Figure 3:
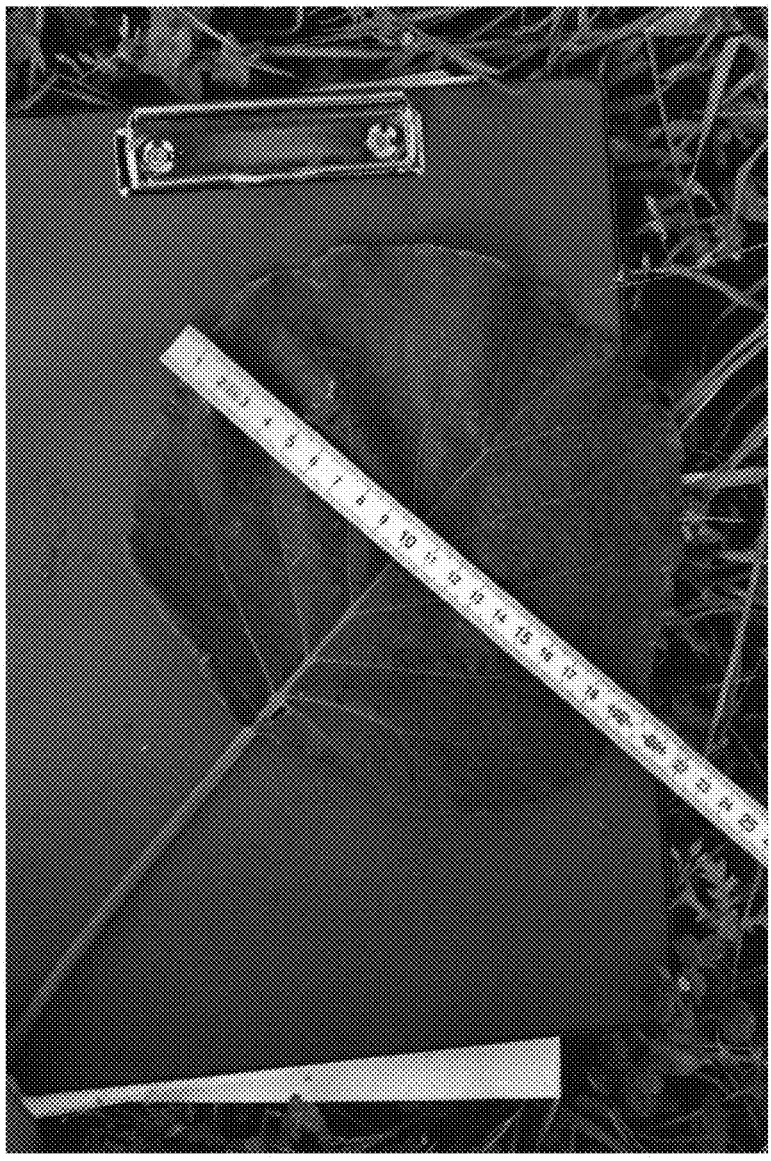
Figure 4:
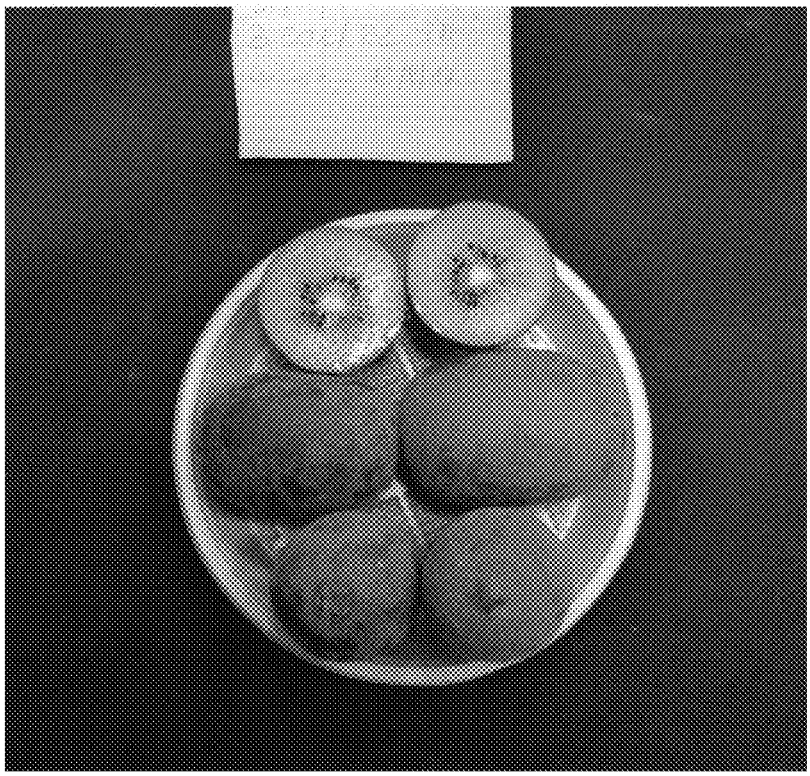

FIG. 1 shows a branch, fruits and leaves of 'AC 501 022';
FIG. 2 shows a shoot and young leaves of 'AC 501 022';
FIG. 3 shows a mature leaf of 'AC 501 022'; and,
FIG. 4 shows whole and sectioned fruit of 'AC 501 022'.

DETAILED BOTANICAL DESCRIPTION

The plants depicted and described herein were planted in 2010 on their own roots at Bernalda-Metaponto, Matera, Italy. Photographs were taken in 2017, and observations were recorded from 2012 to 2019. This description relies primarily on the observations recorded in 2018 and 2019. Colors are described with reference to The Royal Horticultural Society Mini Colour Chart (2005). The characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Plant:
*Plant sex.*—Female.
*Plant form.*—Climbing vine.
*Self-fruit setting.*—Absent.
*Plant vigor.*—Strong.
*Height of mature plant.*—Approximately 3 m from ground to top of canopy.
*Spread of mature plant.*—Approximately 6 $m^2$.

Stem:
*Thickness.*—Medium, 10 mm to 12 mm.
*Color of shoot on sunny side.*—Purple brown 166A.
*Texture of bark.*—Smooth.
*Pubescence on stem.*—Absent or sparse, fine.
*Size of lenticels.*—Small, oblong, 1.0 mm×0.6 mm.
*Color of lenticels.*—Purple brown 166A.
*Number of lenticels.*—Medium, about 6 per $cm^2$.
*Prominence of bud support.*—Very weak.
*Presence of bud cover.*—Absent.
*Size of hole in bud cover.*—Medium.
*Leaf scar.*—Moderately depressed.
*Pith.*—Lamellate.

Young shoot:
*Length.*—Variable.
*Diameter.*—6 mm at 0.3 m below shoot tip.
*Color.*—Yellow green 145B.
*Anthocyanin coloration of growing tip on young shoot.*—Absent or weak.
*Pubescence on young shoot.*—Very sparse.
*Texture of pubescence.*—Soft.

Mature laterals:
*Length.*—Variable.
*Diameter.*—6 mm.
*Color.*—Purple brown 166A.
*Texture.*—Soft.
*Lenticel size.*—0.6 mm.
*Lenticel shape.*—Oblong.
*Lenticel density.*—6 per $cm^2$.

Leaf:
*Arrangement.*—Alternate.
*Shape.*—Orbicular.
*Length.*—175 mm.
*Width.*—186 mm.
*Length/width ratio.*—Intermediate.
*Margin.*—Ciliated.
*Density of serration of margin.*—High.
*Depth of leaf scar.*—Moderately depressed.
*Shape of apex.*—Retuse.
*Basal lobes.*—None.
*Density of hairs on upper side.*—Medium.
*Density of hairs on lower side.*—Sparse.
*Attitude in relation to shoot.*—Upward and outward.
*Color of upper surface.*—Green 137C.
*Color of lower surface.*—Green 194A.
*Anthocyanin coloration of upper side.*—Medium.
*Variegation.*—Absent.
*Venation.*—Reticulate, upper surface central vein pale yellow 161C, upper surface secondary veins and lower surface veins yellow green 145C.
*Leaf texture.*—Tomentose and rugose.
*Petiole length.*—150 mm.
*Petiole diameter.*—3 mm.
*Petiole color.*—Dark pink red 50B.
*Length of petiole relative to blade.*—Large.
*Presence of pubescence on petiole.*—Present, very smooth.

Flowers:
*Time of beginning of flowering.*—6 days before 'Hayward'.
*Duration of flowering.*—4 to 7 days.
*Bud shape.*—Round.
*Bud length.*—2 mm.
*Bud diameter.*—4 mm.
*Bud color.*—Yellow brown N167A.
*Inflorescence type.*—Dichasium.
*Quantity of blossoms per inflorescence.*—Few, avg. 1.0 to 1.3.
*Length of inflorescence.*—34 mm.
*Width of inflorescence at widest point.*—40 mm.
*Peduncle length.*—32 mm.
*Length of lowest lateral.*—18 mm.
*Attitude of lateral in relation to peduncle.*—Open, when present.
*Blossom diameter.*—6 mm.
*Blossom depth.*—3 mm.
*Flower bud.*—Position of first spike — Medium.
*Number of sepals.*—5.
*Sepal length.*—6 mm.
*Sepal width.*—4 mm.
*Sepal margin.*—Entire.
*Sepal color.*—Upper surface — Yellow green 145C.
*Sepal color.*—Lower surface — Brown 199C.
*Density of sepal hairs.*—Absent or sparse.
*Quantity of petals per flower.*—6 to 7.
*Arrangement of petals.*—Overlapping.
*Petal shape.*—Obovate.
*Petal apex.*—Emarginate.
*Petal margin.*—Entire.
*Petal shape in profile.*—Convex.
*Petal color on adaxial side.*—White 155C.
*Petal shading of main color.*—Lighter towards apex.
*Petal color on abaxial side.*—White 155C.
*Pedicel length.*—40 mm.
*Pedicel diameter.*—2 mm.
*Pedicel color.*—Yellow green 145A.
*Pistil quantity per flower.*—30.
*Pistil length.*—11 mm.
*Pistil color.*—White N999D.
*Stigma length.*—1.5 mm.
*Stigma color.*—White N999D.
*Style length.*—8 mm.
*Style color.*—White N999D.
*Ovary length.*—4 mm.
*Ovary diameter.*—6 mm.
*Ovary color.*—Yellow green 145C.
*Anther quantity per flower.*—80 to 90.
*Anther length.*—3 mm.
*Pollen color.*—White 157B Anther color Yellow 12A.
*Pollenizers.*—Belen, Zuva, Matua (not patented).

Fruit:
*Weight.*—Medium, 103 g.
*Length.*—Medium, 74 mm.
*Diameter.*—Medium, 50 mm.
*Length/width ratio.*—Medium.
*Shape.*—Oblong.
*Shape in cross section at median.*—Circular.
*Shape at stylar end.*—Strongly depressed.
*Presence of calyx ring.*—Present.
*Shape of shoulder at stalk end.*—Weakly sloping.
*Length of stalk.*—Medium, 40 mm.
*Diameter of stalk.*—2 mm.

*Color of stalk*.—Brown 199C.
*Length of stalk relative to length of fruit*.—Medium.
*Conspicuousness of lenticels on skin*.—Weak.
*Hairiness of skin*.—Absent.
*Texture of skin*.—Smooth, finely pubescent.
*Color of skin*.—Brown 199C.
*Thickness of skin*.—Thin.
*Adherence of skin to flesh*.—Strong.
*Color of outer pericarp*.—Yellow 7D.
*Color of locules*.—Light yellow brown 160B.
*Diameter of core relative to fruit*.—Small, 12 mm.
*General shape of core in cross section*.—Circular.
*Color of core*.—Light yellow 4D.
*Firmness of flesh*.—0.8+/−0.1 kg/cm$^2$ (8 mm tip, eating ripe).
*Sweetness*.—High, 18.3+/−0.3° Brix (eating ripe).
*Acidity*.—Low.
*Seeds*.—Numerous, oblong, medium reddish brown 200B.
*Time of vegetative bud burst*.—Early, similar to 'Tomua' (U.S. Plant Pat. No. 11,065).
*Time of maturity for harvest*.—Early, September 25 to October 10 (Northern Hemisphere).
*Tolerance to heat, cold, drought*.—Tolerant in area tested (USDA Hardiness Zone 9a/9b); Similar to 'Jintao'.
*Market use*.—Fresh.
*Keeping quality*.—Good.
*Shipping quality*.—Good.

We claim:

1. A new and distinct kiwi plant substantially as described and illustrated herein.

* * * * *